United States Patent [19]
Jaisser et al.

[11] Patent Number: 5,830,729
[45] Date of Patent: Nov. 3, 1998

[54] I SCE I-INDUCED GENE REPLACEMENT AND GENE CONVERSION IN EMBRYONIC STEM CELLS

[75] Inventors: Frederic Jaisser, Malakoff; Michel Cohen-Tannoudji, Paris; Sylvie Robine, Vanves; Andre Choulika, Paris; Daniel Louvard, Sceaux; Charles Babinet, Paris, all of France

[73] Assignees: Institut Pasteur; Institut Curie; Centre National de la Recherche Scientifique, all of Paris, France

[21] Appl. No.: 693,948

[22] Filed: Aug. 7, 1996

Related U.S. Application Data

[63] Continuation of Ser. No. 684,192, Apr. 18, 1996, abandoned.
[51] Int. Cl.$^6$ ..................................................... C12N 15/00
[52] U.S. Cl. ........................ 435/172.3; 435/354; 536/235
[58] Field of Search ............................ 435/172.3, 240.2, 435/320.1, 354; 536/23.1, 23.4, 23.5

[56] References Cited

U.S. PATENT DOCUMENTS 5,474,896  12/1995  Dujon et al. ................................. 435/6

FOREIGN PATENT DOCUMENTS 0 206 849 B1   12/1986   European Pat. Off. .
0 367 666 B1    5/1990   European Pat. Off. .
0 419 621 B1    4/1991   European Pat. Off. .
0 682 111 A1   11/1995   European Pat. Off. .
0 682 112 A1   11/1995   European Pat. Off. .

OTHER PUBLICATIONS

Rousseau–Merck, et al., Human Genetics, vol. 78, pp. 130–133, 1988.

*Primary Examiner*—James Ketter
*Assistant Examiner*—Ivan Yucel
*Attorney, Agent, or Firm*—Finnegan, Henderson, Farabow, Garrett & Dunner, L.L.P.

[57] ABSTRACT

This invention relates to a method of constructing a villin gene hybrid by inserting an I-Sce I restriction site next to or within a gene or cDNA encoding a villin protein. The insertion site of the I-Sce I restriction site is chosen as to provide a first downstream part and a second upstream part from the site, containing at least twelve nucleotides of the gene or cDNA encoding the villin protein. Furthermore, the insertion of the restriction permits a high frequency of homologous recombination events. The villin gene hybrid may be used to transfect eukaryotic cells, and particularly, embryonic stem cells.

8 Claims, 4 Drawing Sheets

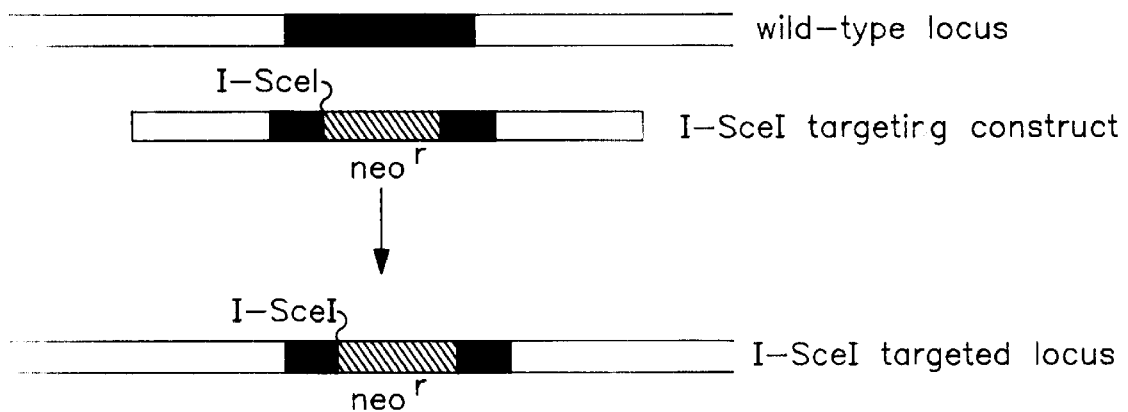
FIG. IA
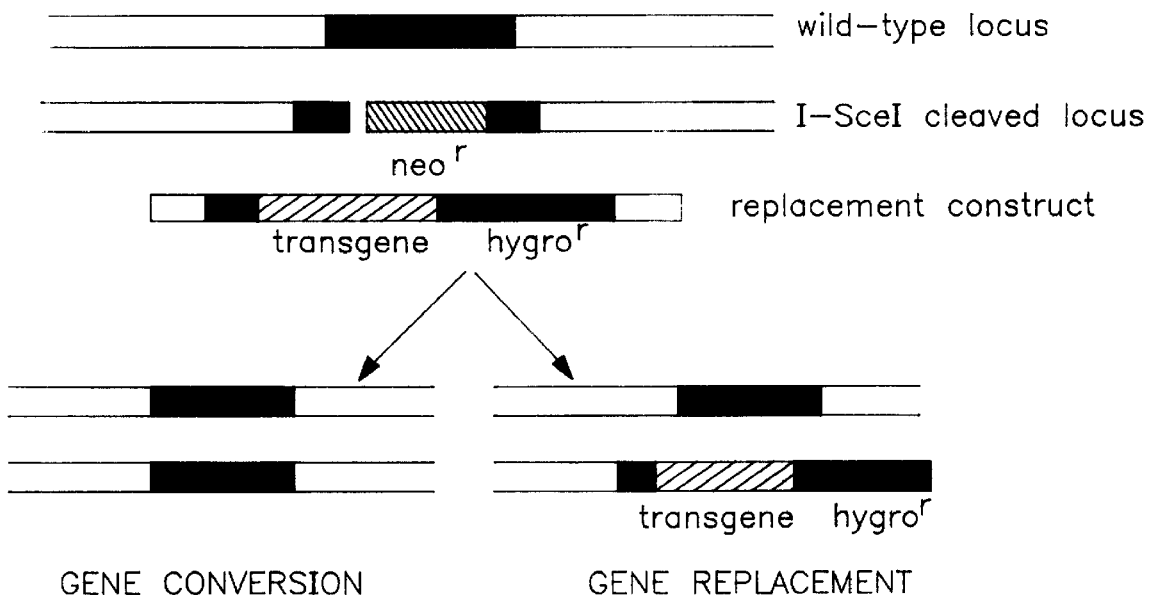
FIG. IB

I SCE I-INDUCED GENE REPLACEMENT AND GENE CONVERSION IN EMBRYONIC STEM CELLS

This application is a continuation of Ser. No. 08/634,192, filed Apr. 18, 1996, now abandoned.

BACKGROUND OF THE INVENTION

The ability to introduce specific alterations of endogenous genes into the germline of mice via targeted mutagenesis in embryonic stem cells (ES) has represented a major breakthrough in mouse genetics. Thus gene inactivation has been widely used to examine the effect of loss of function in various biological processes and has already permitted to accumulate a wealth of new insights into gene function and also to create mouse models of human genetic diseases. However it would also be useful to introduce subtle mutations, in order to refine the genetic analysis and to better approximate the models of genetic diseases which do not necessarily result from null mutations. Thus several strategies have been developed, aimed at generating subtle mutations in a given gene. However, one common limitation to all the current gene targeting procedures is the low frequency of correct targeting, which becomes a serious problems especially when using two successive rounds of targeting. Therefore, efforts have been made to increase the efficiency of gene targeting by several means like increasing the size of the region of homologies with the target locus, using isogenic genomic DNA, or improving the selection procedures.

SUMMARY OF THE INVENTION

In this paper, we present an alternative approach, to overcome these limitations, which relies on the observation that double-strand ends of broken chromosomes are highly recombinogenic; we reasoned that the introduction of a double strand break (DSB) in an endogenous gene could increase targeting frequency through stimulation of the cellular recombination machinery. Thus our approach which involves two steps, is based on the induction of a specific DSB in a natural locus, the gene encoding villin, an actin binding protein mainly expressed in the intestine and kidney Louvard. In a first step, an I-Sce I restriction site is introduced into the villin locus. Indeed, I-Sce I, a very rare cutter endonuclease has been shown to initiate DSB in the mammalian genome, while its random integration allowed new insights into the analysis of recombination mechanisms in mammals. In the second step, the effect of DSB on DNA repair and homologous recombination frequency is assessed after cotransfer of an I-Sce I expressing vector and of a villin replacement vector in the targeted ES cells (FIG. 1). We found that the presence of a DSB in the target gene not only enhanced homologous replacement by the incoming DNA but also induced gene conversion at a very high rate.

BRIEF DESCRIPTION OF THE DRAWINGS

FIG. 1 Strategy for the induction of gene conversion and gene replacement upon DSB repair in the natural villin locus. (A) Gene targeting of the I-SceI restriction site in the villin locus by homologous recombination (B) Co-transfection of the pI-SceI expression plasmid and of the replacement construct conferring hygromycine resistance. Resulting recombinants represent gene conversion events, with return to the wild-type genotype, or homologous gene replacement in the villin locus.

DETAILED DESCRIPTION

Figure 2A:
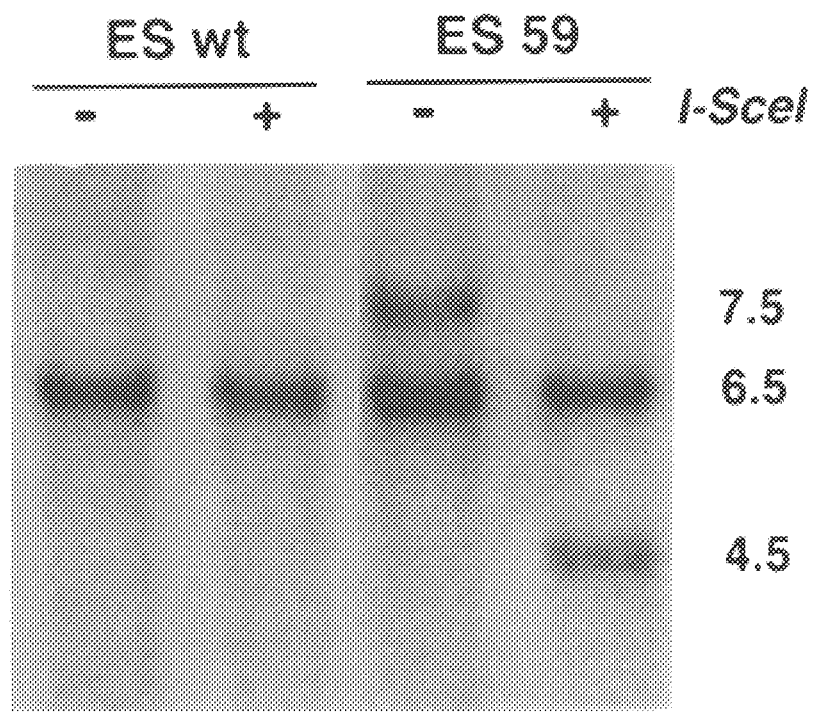
FIG. 2 Southern blot analysis of gene targeting of the I-SceI restriction site in the villin locus. Experiments were performed as described in ref X. (A). Targeting of the I-SceI restriction site in the villin locus of CK35 ES cells. Genomic DNAs of ES WT and ES59 clone were digested with (lanes 2 and 4) or without (lanes 1 and 3) the I-SceI meganuclease, followed by ScaI digestion and probed with A (0.4 kb BamHI-HincII, 3' external probe). The 7.5 kb band represents the targeted allele that resulted in a 4.5 kb band when digested by I-SceI. (B) Restriction maps for (from top to bottom) the 3' portion of the mouse villin locus, the targeting construct, the homologous recombinant. The dark rectangles represent the three first exons of the villin gene. The black bar represents the probe A used for hybridization. Restriction sites of Sca I (S), BamHI (B) and I-SceI are indicated. Numbers on the right side of the blot indicates the sizes of the bands in kb.

Eight independent ES clones were correctly targeted with the I-Sce I targeting construct, as demonstrated by Southern blot analysis (data not shown). ES clone #59 was extensively characterized, showing homologous integration of the I-Sce I-neo gene into the 2nd exon of villin (FIG. 2A). This analysis also showed that the meganuclease I-Sce I is able to specifically cleave the targeted allele in vitro (FIG. 2A, lane 3).

The ES 59 clone was then used in the second step. Double-strand breaks were induced by I-Sce I digestion after transient transfection of the ES cells with an expression vector for I-Sce I meganuclease (pI-Sce I). Cotransfection of these vectors was performed with the gene replacement construct pvillin-LacZ (ref methods). ES clones were selected for Hygromycine resistance and subsequently screened for neomycine sensitivity in order to recover clones which undergo modification of the I-SceI-Neo allele. Results obtained in different experimental conditions are illustrated on table 1. In these experiments, we used the pvillin-lacZ construct either in circular form or excised from the plasmid backbone and we varied the amount of I-Sce I expressing vector. Interestingly it appeared that the number of clones with the expected phenotype (Hygro$^R$, G418$^S$) was dependent on the quantity of pI-Sce I expression vector used for electroporation (table 1). With low quantity (5 μg) of pI-Sce I plasmid, 10% of the recovered Hygro$^R$ clones died in G418 medium; in contrast, when high quantity (30–50 μg) were used, the level raised up to 50% of the clones being sensitive to G418. These observations suggest that I-Sce I endonuclease is actually able to cleave its site in vivo at the villin locus and that this stimulates the loss or the inactivation of the Neo gene from the I-Sce I-targeted villin allele.

Figure 2B:
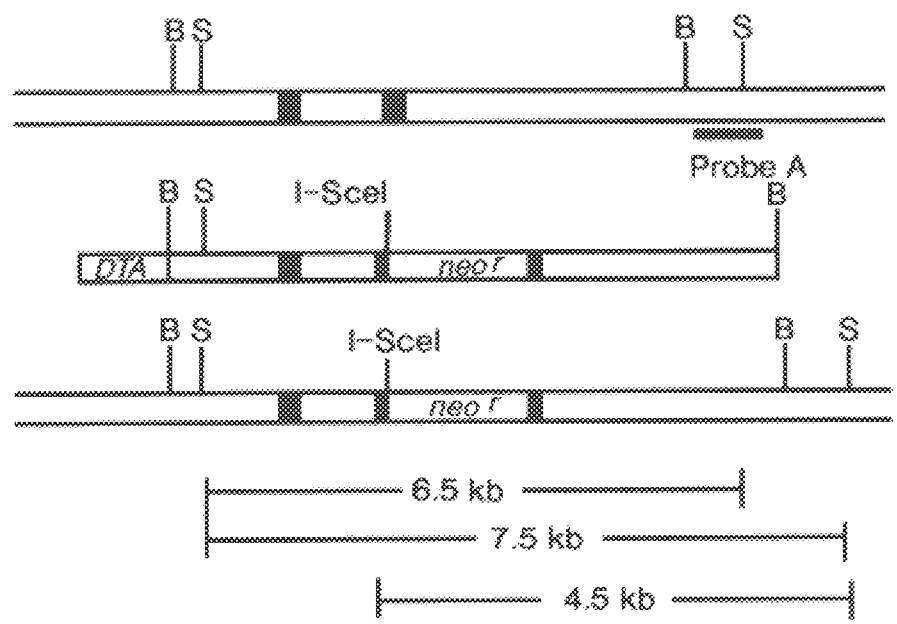
Figure 3A:
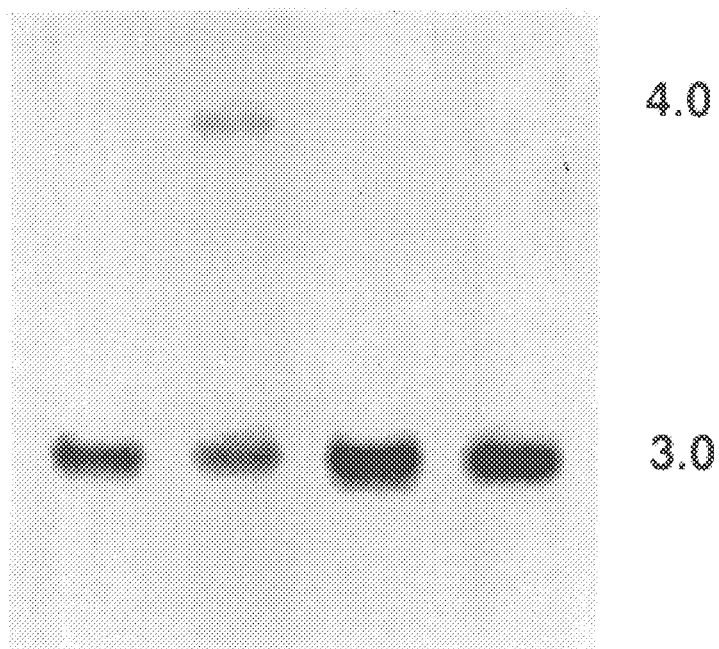
FIG. 3 Southern blot analysis showing homozygotization of the targetted villin locus after I-SceI meganuclease expression. (A) Genomic DNAs of ES WT, ES59, ES348 and ES345 clones were digested with ScaI and probed with B (0.8 kb SmaI-HindIII, internal probe). The 4.0 kb band represents the I-SceI-neo targeted allele that resulted in a 3.0 kb band after I-SceI expression, due to reversion to a WT genotype by gene convertion. (B) Restriction maps for (from top to bottom) the 3' portion of the mouse villin locus, the I-SceI-targeted locus, the converted recombinant. Restriction sites of Hind III (H) is indicated. The black bar represents the probe B used for hybridization. (C) FISH analysis of converted ES clone 313, showing the presence of two villin loci.
Figure 3B:
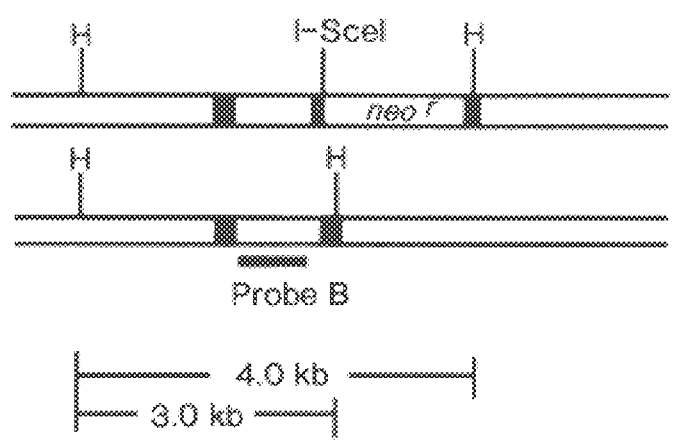

The genomic structure of the villin alleles in the Hygro$^R$/G418$^S$ clones was analysed by Southern blot. Surprisingly, in a vast majority of the clones (80–100%), only the wild-type villin alleles could be detected (table 1; FIG. 2). Such finding could be explained by different mechanisms. A trivial explanation could be a contamination of the original ES 59 clone by wild-type cells. However this possibility was ruled out by PCR analysis of ES 59 subclones obtained by limit. Similarly, the possible loss of the I-SceI targeted villin allele during the selection step was eliminated by FISH analysis. (FIG. 3, panel C). Furthermore, Southern blot analysis of the genomic region surrounding the Kpn I site in which the I-Sce I-neo cassette was inserted in the parental ES 59 clone (ref. methode) indicated that no aberrant rearrangement occured at the villin locus. Taken together, these results indicate that two wild-type villin alleles were present in these cells and therefore strongly suggest that allelic conversion has taken place after transient expression of I-SceI in ES 59 cells.

Thus, the predominant repair mechanism of site directed DSB at the villin locus in a mitotic cell line is an interchromosomal gene conversion. This allelic conversion results in the homozygotization of the villin locus, indicating that the unbroken wild-type locus is used as a repair matrix for the broken chromosome. Gene conversion after induction of a DSB has been observed in yeast and in Drosophila [Fairhead, 1993 #13; Mezard, 1994 #14; Shulman, 1995 #15]. In mammalian cells, interchromosomal recombination has been previously reported to be suppressed in somatic cells [Shulman, 1995 #13; Godwin, 1994 #16]. This contrasts with what is observed in meiotic cells during mouse spermatogenesis (Murti 92) or in totipotent ES cells, as reported here. It should be noted that previous studies on the repair of I-Sce I induced DSB in mammalian cells have not reported such events [Rouet, 1994 #11 and 12; Lukacsovich, 1994 #17]. This is probably due to the experimental procedure which counterselected against this kind of event, leading to the loss of the selectable marker. The I-Sce I experimental strategy used in this study would therefore be useful for the detailed analysis of gene conversion mechanisms in mammalian cells and would be particularly powerful when using a cell line with defined polymorphism and around the I-SceI-targeted locus. Induction of specific DSB in a natural locus in mice derived from I-SceI targeted ES cells should also allow homozygotization of any endogenous locus in various somatic cells in vivo. Such homozygotization could be controlled either spatially or temporally, by the use of appropriate regulatory sequences to direct I-SceI meganuclease expression. This may help to understand the functional significance of gene polymorphisms and genomic imprinting, for example, in higher eucaryotes.

Whereas gene conversion was the only event observed when the excised pvillin-nlsLacZ construct was used, both gene conversion and gene targeting were observed with supercoiled plasmid (table 1). Four of the 24 Hygro$^R$/G418$^S$ clones (17%) of Experiment 3 exhibited the restriction pattern expected for an homologous recombination event between the pvillin-nlsLacZ replacement construct and the I-Sce I-targeted villin allele. Two of these clones were extensively characterized. As shown in FIG. 3, the nlsLacZ gene was correctly integrated in the villin locus in both ES clones 321 and 323. In these clones, no random integration of the pvillin-nlsLacZ or pI-SceI constructs was observed. Three other clones contained both a wild-type and an abnormal allele, corresponding to the aberrant integration of the I-SceI expression plasmid in the villin locus (data not shown). This may be due to the presence of SV40-polyA homologous sequences in both the neo and pI-SceI cassettes. Spontaneous targeting of the pvillin-nlsLacZ replacement construct in the wild-type allele of the ES 59 cells has never been observed. Altogether, these results indicate that a high homologous recombination frequency can be obtained through cotransfection of pI-Sce I expressing vector and a villin replacement vector in a circular form, allowing specific introduction of extrachromosomal DNA in the targeted locus. Furthermore it should be noted that the homologous recombination frequency we have observed is probably underestimated because in these experiments not every cell received both constructs. Indeed, we found that the I-SceI-targeted villin locus of Hygro$^R$/G418$^R$ clones could still be cleaved in vitro with I-SceI (data not shown). Moreover, the quantity of replacement construct we have electroporated may be limiting. Higher efficiency may be obtained by including the CMV-I-SceI cassette into the replacement vector and transfecting ES cells with higher quantity of the replacement construct. The reason why recombination with the donor plasmid occurs at a high frequency when the plasmid is supercoiled, while it is nor efficient when the plasmid is linearized, is unclear. It may rely on the mechanistic of the double-strand break gap repair event [Resnick, 1976 #18, Szostak, 1983 #19].

Figures 4A, 4B:
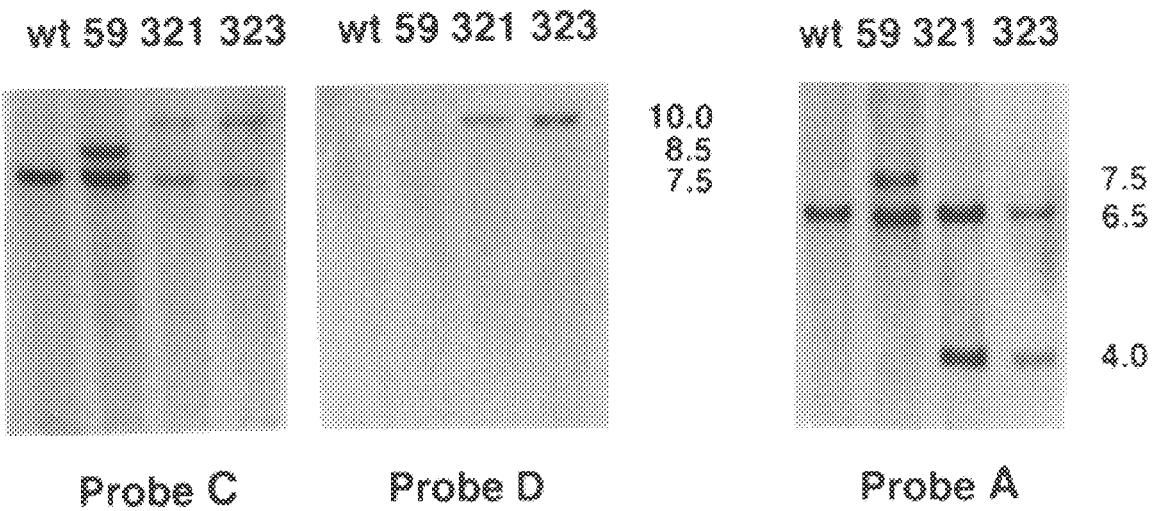
FIGS. 4A–4C Gene replacement of the I-SceI targeted villin locus after I-SceI meganuclease expression (A) Genomic DNAs of ES WT, ES59, ES321 and ES323 clones were digested with BglI and probed with C (0.5 kb BglII-StuI, 5' external probe) and D (3 kb, lacZ probe). The 7.5 kb band represents the I-SceI targeted allele that resulted in a 10.0 kb band after I-SceI expression, due to homologous intergration of LacZ and Hygro in the I-SceI targeted allele. (B) Genomic DNAs of ES WT, ES59, ES321 and ES323 clones were digested with ScaI and probed with A (0.4 kb BamHI-HincII, 3' external probe). The 7.5 kb band represents the I-SceI targeted allele that resulted in a 4.0 kb band after I-SceI expression, due to homologous integration of LacZ and Hygro. (C) Restriction maps for (from top to bottom) the 3' portion of the mouse villin locus, the I-SceI-targeted locus, the homologous recombinant. Restriction sites of BglII (Bg), Sca I (S) and I-SceI are indicated. The black bars represent the probes C, D and A used for hybridization. (D) Immunolocalizaton of villin and lacZ in embryoid bodies obtained after in vitro differentiation of ES 321 cells showing expression of LacZ in villin-expressing cells.
Figure 4C:
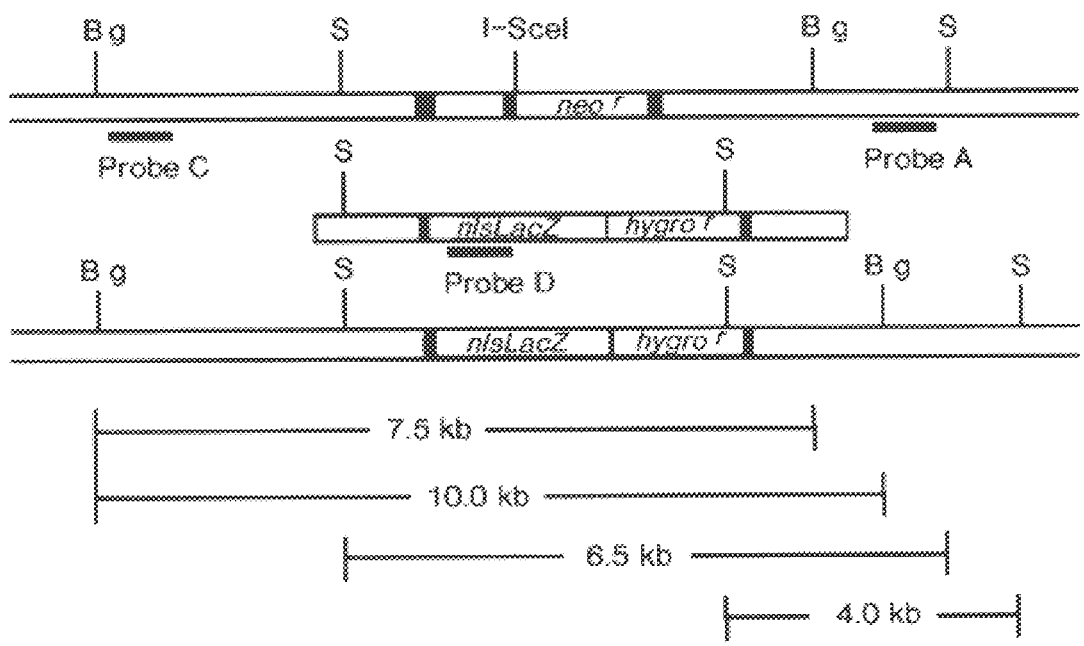

Introduction of I-Sce I in mammalian cells is apparently non-toxic. The 18 bp I-SceI restriction site, on stastitical grounds, should not be present in the mammalian genome. However, even if I-SceI induces a DSB elsewhere in the genome, it would probably be repaired by interchromosomal gene conversion, as demonstrated here at the villin locus. After transient expression of I-SceI, no obvious effects were observed in ES cells. I-SceI transfected ES cells formed apparently normal embryoid bodies after in vitro differentiation. Furthermore, the villin-lacZ allele appeared to be expressed normally in a cell specific way: indeed, in keeping with the known expression of villin in the visceral endoderm cells of the implanting embryo and of EC derived embryoid bodies, we could show by immunolocalization that β-gal and villin colocalized in and were restricted to the endoderm cells of the embryoid bodies derived from ES clone 321 (see FIG. 4, panel D). This demonstrates that the nls-lacZ gene is actually under the control of the villin regulatory sequences. Chimeric animals (50–80% chimerism) have been obtained after microinjection of ES 321 cells in blastocysts. Crosses are underway to test germ line transmission of the targeted ES cells.

Our data indicates that the introduction a site-specific DSB in a natural locus allows gene targeting with high frequency. By contrast to other gene targeting procedures [Askew, 1993 #1; Hasty, 1991 #2; Gu, 1994 #3; Stacey, 1994 #4], the modified target locus is altered such that the endogenous repair machinery can be stimulated. This helps to overcome the major limitation of the gene targeting procedure, i.e. the low frequency of adequate gene targeting, especially when various mutations of the same locus are needed. Moreover, due to the mechanism of integration of the extrachromosomal DNA, i.e. DSB repair, the replacement construct needs smaller regions of homologies with the target locus than in classical gene targeting procedure [Lin, 1990 #21; Lin, 1990 #22; Ayares, 1986 #23]. In addition, as chromosomal DSB is repaired in regard to the unbroken matrix, any modification present in the replacement vector will be copied into the target locus. Therefore, this approach offers an efficient way to introduce subtle mutations at a desired location in the genome.

Unlike the Cre-loxP system of the P1 bacteriophage (for review: [Kilby, 1993 #24; Sauer, 1994 #25], the I-Sce I meganuclease system is not a recombinase system. I-Sce I does not control the formation and the resolution of DNA synapsis but relies on the endogenous cellular repair machinery. The recombination process induced by I-Sce I is irreversible since the I-Sce I recognition site is not restored after recombination allowing stable integration of foreign sequences, a process that is not possible using the the Cre-loxP system.

TABLE 1

Number and genotype of independent ES clones isolated in different experiments (E 1–3).
Ratio of pI-Sce I/pvillLacZ used for ES cell transfection and sensitivity to selection markers are indicated.

| | Ratio pI-Sce I/ pvill-LacZ | HygroR | HygroR NeoS | Allelic convertion | Gene replacement |
|---|---|---|---|---|---|
| E1 pvill-LacZ excised | 1/1 | 80 | 8 | 8 | 0 |
| E2 pvill-LacZ excised | 6/1 | 56 | 36 | 36 | 0 |
| E3 pvill-LacZ supercoiled | 10/1 | 55 | 24 | 17 | 4 |

This invention will be described in greater detail in the following Examples.

EXAMPLE 1

Gene targeting of the I-Sce I restriction site in the murine villin gene

An I-Sce I restriction site was introduced in a unique Xho I site flanking the 5' end of the Neo resistance gene (pMCl, Stratagene) using an oligodimer (sens oligo; antisens oligo), disrupting the Xho I site. This I-Sce I/Neo gene was introduced in a unique Kpn I site present in a 6 kb BamHI fragment isolated from a λDASHII phage containing 16 kbp of the mouse villin gene (kind furnished by G. Tremp, ROR) and subcloned in pBS/KS+. The 1.2 kb DT-A cDNA (kindly provided by S. Tashbak) was subcloned in the unique Xho I site flanking the 5' end of the construct 2. $10^7$ CK35 ES cells (cohen-tannoudji, 95) were electroporated with 20 μg of the Pvu I-linearized targeting construct. G418 (300 μg/ml) was added 36 hours after plating. G418-resistant clones were isolated and their genotype analysed by Southern blot.

In order to exclude heterogeneity of the homologous recombinant ES clone 59, we performed PCR analysis of ES 59 subclones obtained by limit dilution of the parental ES 59 clone: the presence of the neo gene was observed in all the 30 independent subclones tested.

EXAMPLE 2

I-Sce I mediated gene conversion and gene replacement

A 5' 2 kb BamH I-Nco I villin gene fragment (located upstream of the initiation codon) was subcloned in front of the nlsLacZ coding sequences (kindly furnished by Sharagim). A 3'1.6 kb Hind III-Xba I villin gene fragment was subcloned downstream of the PGK-Hygromycin resistance gene (kindly given by S. Memet). The Hygro- 3' villin fragment was then subcloned in the unique Spe I site downstream of the 5' villin-nlsLacZ construct. The supercoiled pI-Sce I expression plasmid () and the pvillin nlsLacZ replacement construct were electroporated into ES 59 cells following the different conditions summarized in table 1. Hygromycin (150 μg/ml) was added 36 hours after plating for 6 days. Mitomycine-C-treated $G418^R$ primary fibroblasts were added three times during the selection period. Hygromycine-resistant ES clones were isolated and amplified in ES medium. Duplicate cultures were prepared to screen for G418-sensitive and Hygromycin-resistant ES clones.

EXAMPLE 3

In vitro ES cell differentiation and immunocytochemistry $10^6$ ES cells were plated in sterile Petri dishes in 10 ml of culture medium (DMEM, 10% FCS,) without LIF nor β-mercaptoethanol. The majority formed aggregates floating in the medium 6–10 days after plating, embryoid bodies were collected for subsequent analysis. After fixation with paraformaldehyde ?%, embryoid bodies were embedded in x% gelatin and cutted in & uM sections. Immunocytochemistry were performed using a polyclonal villin antibody () and a β-gal xx antibody ().

The following references describe the state of the art. The entire disclosure of each reference is relied upon and incorporated by reference herein.

European Patents: 367 666 (B1) and 206 849 (B2) of Louvard et al. concerning the villin gene and its promoter.

U.S. Pat. No. 5,474,896 of Dujon et al. concerning the nucleotide sequence encoding the enzyme I-Sce I.

European Patent: 419 621 (B1) and European Patent Applications: 682,111 (A1) and 682,112 (A1) concerning the "Knock in" method.

Choulika et al., Mol. and Cell. Biol., 15:1968–1973 (April 1995), which describes induction of homologous recombination in mammalian chromosomes by using the I-Sce I system of S. cerevisiae.

Choulika et al., C. R. Acad. Sci. Paris, 317:1013–1019 (1994), which describes yeast I-Sce meganuclease induction of site-directed chromosomal recombination in mammalian cells.

This invention thus relates to the transfection of ES cells by a plasmid containing a construct comprising the villin gene (human or murine) in which is inserted a nucleotide sequence recognized by the restriction enzyme I-Sce I. The ES cells are able to be later transfected by a plasmid containing the gene coding for the enzyme I-Sce I, itself recombinant. Any eukaryotic cells or cell line, which will be transfected by a plasmid containing the villin gene or a part of the cDNA coding for the villin protein and the nucleotide sequence recognized by the I-Sce I restriction enzyme, is a part of the invention. The use of such recombinant cells is to obtain the expression of a protein of interest after transfection by a first plasmid carrying the corresponding nucleotide sequence of interest and a second plasmid carrying the gene coding for I-Sce I. The articles of Choulika et al. cited herein, describe the technique that can be used to construct such cells.

In conclusion, we have constructed an embryonic stem cell line carrying the recognition site of the I-Sce I meganuclease into a natural locus, i.e. the villin gene. We show in this paper that allelic conversion occurs in mammalian cells to allow specific double-strand break repair after I-Sce I-mediated DSB. Moreover, the yeast I-Sce I endonuclease can specifically induce gene targeting and homologous recombination events with high frequency, allowing specific and highly efficient gene replacement in embryonic stem cells. The use of I-SceI alone or in combination with other systems like Cre-loxP in gene targeting experiments will greatly facilitate the obtention of the various mutations needed for a comprehensive analysis of gene function. One particularly promising development of this novel gene targeting strategy could be in ovo I-SceI-mediated gene replacement. This would considerably alleviate the process of targeted genetic manipulation of the mammalian genome.

Following are citations of references identified in this application. The entire disclosure of each reference is relied upon and incorporated by reference herein.

1. G. R. Askew, T. Doetschman, J. B. Lingrel, *Mol Cell Biol* 13, 4115 (1993).

2. P. Hasty, S. R. Ramirez, R. Krumlauf, A. Bradley, *Nature* 350, 243 (1991).

3. H. Gu, J. D. Marth, P. C. Orban, H. Mossmann, K. Rajewsky, *Science* 265, 103 (1994).

4. A. Stacey, et al., *Mol Cell Biol* 14, 1009 (1994).

5. F. L. Lin, K. Sperle, N. Sternberg, *Mol. Cell Biol.* 4, 1020 (1984).

6. W. D. Heyer, R. D. Kolodner, *Prog Nucleic Acid Res Mol Biol* 46, 221 (1993).

7. M. M. Seidman, *Mol. Cell. Biol.* 7, 3561 (1987).

8. A. Jacquier, B. Dujon, *Cell* 41, 383 (1985).

9. A. Choulika, A. Perrin, B. Dujon, J. F. Nicolas, *C. R. Acad. Sci. Paris* 317, 1013 (1994).

10. A. Choulika, A. Perrin, B. Dujon, J. F. Nicolas, *Mol. Cel. Biol.* 15, 1968 (1995).

11. P. Rouet, F. Smith, M. Jasin, *Mol. Cell. Biol.* 14, 8096 (1994).

12. P. Rouet, F. Smith, M. Jasin, *Proc. Natl. Acad. Sci. U.S.A.* 91, (1994).

13. C. Fairhead, B. Dujon, *Molecular general genetics* 240, 170 (1993).

14 C. Mezard, A. Nicolas, *Molecular and cellular biology* 14, 1278 (1994).

15. M. J. Shulman, C. Collins, A. Connor, L. R. Read, M. D. Baker, *Embo J* 14, 4102 (1995).

16. A. R. Godwin, R. J. Bollag, D. M. Christie, R. M. Liskay, *Proc Natl Acad Sci USA* 91, 12554 (1994).

17. T. Lukacsovich, D. Yang, A. S. Waldman, *Nucleic Acids Res* 22, 5649 (1994).

18. M. A. Resnick, P. Martin, *Mol. Gen. Genet.* 143, 119 (1976).

19. J. W. Szostak, T. L. Orr-Weaver, R. I. Rothstein, *Cell* 33, 25 (1983).

20. R. Maunoury, et al., *Embo J* 7, 3321 (1988).

21. F. L. M. Lin, K. Sperle, N. Sternberg, *Mol. Cell Biol.* 10, 103 (1990).

22. F. L. Lin, K. Sperle, N. Sternberg, *Mol Cell Biol* 10, 113 (1990).

23. Ayares, *PNAS* 83, 5199 (1986).

24. N. J. Kilby, M. R. Snaith, J. A. H. Murray, *TIGs* 9, 413 (1993).

25. B. Sauer, *Current Opinion in Biotechnology* 5, 521 (1994).

What is claimed is:

1. A method of making a villin gene hybrid containing a locus for homologous recombination, wherein the method comprises inserting an I-SceI restriction site adjacent to or within a villin gene or cDNA encoding villin protein, such that at least a portion of the locus for homologous recombination is contained within the villin gene or cDNA encoding villin protein, and wherein said locus comprises the I-SceI restriction site and at least twelve nucleotides upstream and downstream of the I-SceI restriction site providing homology for homologous recombination.

2. The method of claim 1, which comprises creating a double-stranded break at the I-SceI restriction site with an I-SceI meganuclease.

3. The method of claim 1, which comprises inserting DNA at the double-stranded break in the villin gene or cDNA encoding the villin protein by homologous recombination.

4. The method of claim 1, wherein the I-SceI restriction site is in the second exon of a villin gene or cDNA encoding the villin protein or in an intronic region of a villin gene.

5. The method of claim 3, wherein the homologous recombination is in an eukaryotic host cell.

6. The method of claim 5, wherein the eukaryotic host cell is an ES cell.

7. A hybrid nucleotide sequence comprising an I-SceI restriction site adjacent to or within a villin gene or cDNA encoding a villin protein, such that at least a portion of a locus for homologous recombination is contained within the villin gene or cDNA encoding villin protein, wherein said locus comprises the I-SceI restriction site and at least twelve nucleotides upstream and downstream of the I-SceI restriction site.

8. The hybrid nucleotide sequence of claim 7, which contains a selective marker adjacent to the I-SceI restriction site.

* * * * *